US00PP16789P2

(12) United States Plant Patent
Farrell

(10) Patent No.: US PP16,789 P2
(45) Date of Patent: Jul. 11, 2006

(54) ***EUONYMUS* PLANT NAMED 'MICKAELA'**

(50) Latin Name: *Euonymus fortunei*
Varietal Denomination: Mickaela

(75) Inventor: Val Farrell, Dublin (IE)

(73) Assignee: Witteman & Co., Hillegom (NL)

( * ) Notice: Subject to any disclaimer, the term of this patent is extended or adjusted under 35 U.S.C. 154(b) by 38 days.

(21) Appl. No.: 11/073,490

(22) Filed: Mar. 5, 2005

(51) Int. Cl.
*A01H 5/00* (2006.01)

(52) U.S. Cl. ..... Plt./246

(58) Field of Classification Search ..... Plt./246
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Euonymus* plant named 'Mickaela', characterized by its uniform, compact, mounded and procumbent plant habit; freely branching growth habit; and distinct yellow and green variegated leaves.

1 Drawing Sheet

Botanical designation: *Euonymus fortunei.*
Cultivar denomination: 'Mickaela'.

BACKGROUND OF THE INVENTION

The present Invention relates to a new and distinct cultivar of *Euonymus* plant, botanically known as *Euonymus fortunei,* and hereinafter referred to by the name 'Mickaela'.

The new *Euonymus* is a naturally-occurring branch mutation of the *Euonymus fortunei* cultivar Sunspot, U.S. Plant Pat. No. 4,340. The new *Euonymus* was discovered and selected by the Inventor in a controlled environment in Rathmooney, Skerries, County Dublin, Ireland in 1993. The new *Euonymus* was selected on the basis of its unique leaf coloration.

Asexual reproduction of the new cultivar by cuttings since 1995 in Rathmooney, Skerries, County Dublin, Ireland, has shown that the unique features of this new *Euonymus* are stable and reproduced true to type in successive generations.

SUMMARY OF THE INVENTION

Plants of the cultivar Mickaela have not been observed under all possible environmental conditions. The phenotype may vary somewhat with variations in environment such as temperature and light intensity without, however, any variance in genotype.

The following traits have been repeatedly observed and are determined to be the unique characteristics of 'Mickaela'. These characteristics in combination distinguish 'Mickaela' as a new and distinct *Euonymus* cultivar:

1. Uniform, compact, mounded and procumbent plant habit.
2. Freely branching growth habit.
3. Distinct yellow and green variegated leaves.

Plants of the new *Euonymus* are most similar to plants of the parent, the cultivar Sunspot. In side-by-side comparisons conducted in Hillegom, The Netherlands, plants of the new *Euonymus* differed from plants of the cultivar Sunspot in the following characteristics:

1. Plants of the new *Euonymus* were more uniform than plants of the cultivar Sunspot.
2. Plants of the new *Euonymus* had shorter internodes and are more compact than plants of the cultivar Sunspot.
3. Plants of the new *Euonymus* had larger leaves than plants of the cultivar Sunspot.
4. Plants of the new *Euonymus* had more distinct and contrasting leaf variegation and brighter leaf coloration than plants of the cultivar Sunspot.

Plants of the new *Euonymus* can be compared to plants of other cultivars of *Euonymus* known to the Inventor. Plants of the new *Euonymus* differ from plants of other cultivars known to the Inventor in the following characteristics:

1. Plants of the new *Euonymus* are more uniform than plants of other cultivars of *Euonymus* known to the Inventor.
2. Plants of the new *Euonymus* have more distinct and contrasting leaf variegation and brighter leaf coloration than plants of other cultivars of *Euonymus* known to the Inventor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Euonymus.*

The photograph at the top of the sheet comprises a side perspective view of a typical flowering plant of 'Mickaela' grown in a container.

The photograph at the middle of the sheet is a close-up view of a typical stem and leaves of 'Mickaela'.

The photograph at the bottom of the sheet is a close-up view of typical leaves of 'Mickaela'.

DETAILED BOTANICAL DESCRIPTION

Plants shown in the aforementioned photographs and used in the following description were grown in containers under conditions which closely approximate commercial production conditions during the early spring in an outdoor nursery in Boskoop, The Netherlands. Plants in the photographs and those used for the description were about four years old when the photographs and description were taken. During the production of the plants, day temperatures ranged from 3 to 15° C. and night temperatures ranged from −2 to 9° C. In the following description, color references are made to The Royal Horticultural Society Colour Chart, 2001 Edition, except where general terms of ordinary dictionary significance are used.

Botanical classification: *Euonymus fortunei* cultivar Mickaela.

Parentage: Naturally-occurring branch mutation of the *Euonymus fortunei* cultivar Sunspot, not patented.

Propagation:

*Type.*—By cuttings.

*Time to initiate rooting, summer.*—About four weeks at 20° C.

*Time to produce a rooted young plant, summer.*—About three months at 18° C.

*Root description.*—Moderately thick; creamy white in color.

*Rooting habit.*—Moderately dense.

Plant description:

*Plant and growth habit.*—Perennial. Uniform, compact, mounded and procumbent plant habit. Freely branching habit; about 17 lateral branches per plant; with short internodes; dense and bushy plant habit; moderately vigorous growth habit.

*Growth rate.*—Moderate growth rate; about one year is required to produce fully-grown plants.

*Plant height.*—About 19 cm.

*Plant width.*—About 67 cm.

*Lateral branch description.*—Length: About 16 cm. Diameter: About 3 mm. Internode length: About 1.4 cm. Strength: Strong. Texture: Young stems, smooth and glabrous; older stems, woody, rough. Color: Young stems, 8A, with development, 144B; older stems, N200A to N200B.

*Foliage description.*—Arrangement: Opposite, simple. Length: About 4 cm. Width: About 2.3 cm. Shape: Ovate to elliptic. Apex: Obtuse. Base: Attenuate. Margin: Crenate. Texture, upper and lower surfaces: Smooth, glabrous. Venation pattern: Pinnate.

*Color.*—Developing foliage, upper surface: Central area, N144B; towards the margin, darker than 143A. Developing foliage, lower surface: Central area, N144B; towards the margin, darker than 143B to 143C. Fully expanded foliage, upper surface: Central area, 10A to 10B occasionally 9A to 9B; towards the margin, slightly darker and duller than 139A; venation, 10A to 10B or similar to lamina. Fully expanded foliage, lower surface: Central area, 10C; towards the margin, 143B to 143C; venation, 9A or similar to lamina.

*Petiole length.*—About 5 mm.

*Petiole diameter.*—About 1.5 mm.

*Petiole texture, upper and lower surfaces.*—Smooth, glabrous.

*Petiole color, upper and lower surfaces.*—10C.

Flower description: Flower development on plants of the new *Euonymus* has not been observed.

Disease/pest resistance: Plants of the new *Euonymus* have not been noted to be resistant to pathogens and pests common to *Euonymus*.

High temperature tolerance: Plants of the new *Euonymus* have been observed to tolerate temperatures of 35° C.

Hardiness: Plants of the new *Euonymus* are hardy to USDA Zone 6.

It is claimed:

1. A new and distinct cultivar of *Euonymus* plant named 'Mickaela', as illustrated and described.

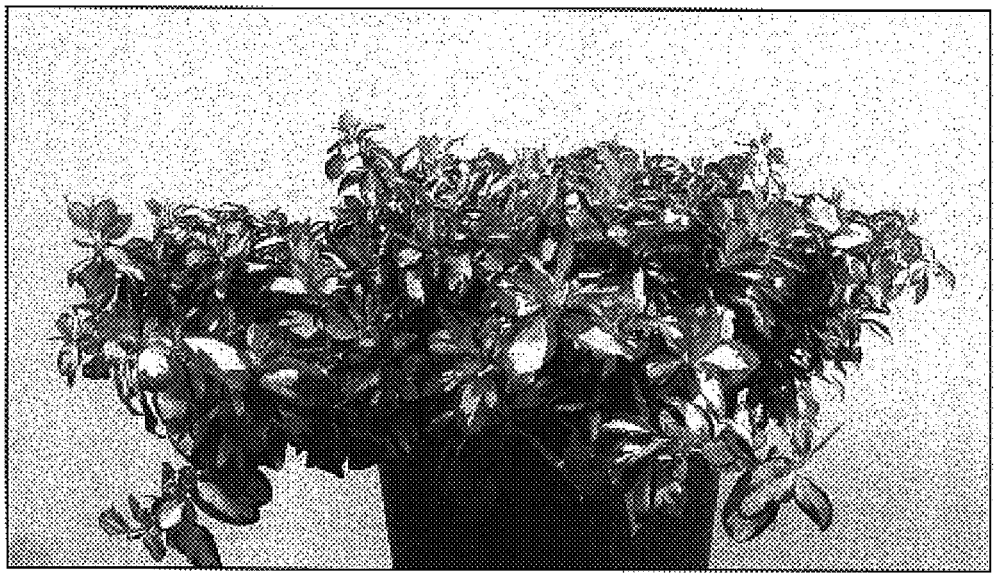
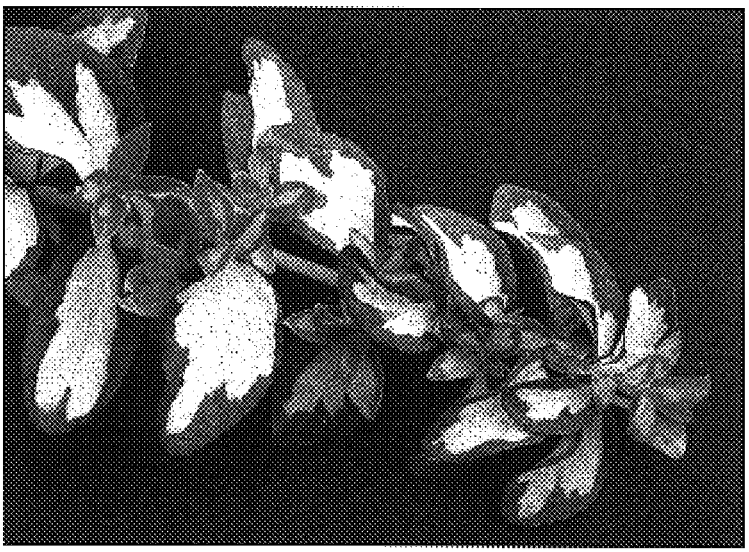
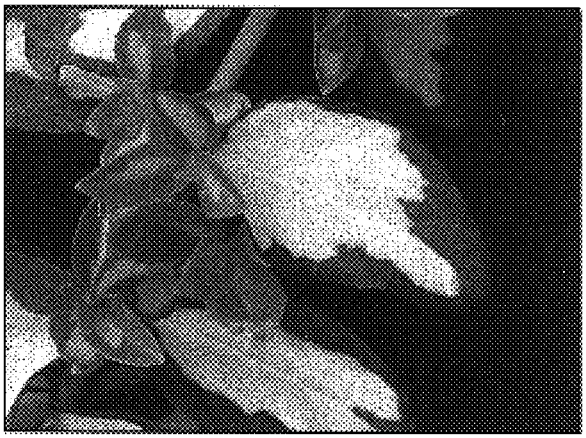

* * * * *